United States Patent [19]

Wechsler

[11] Patent Number: 4,873,872

[45] Date of Patent: Oct. 17, 1989

[54] FLOAT FOR FLUID MEASUREMENTS

[76] Inventor: Lawrence I. Wechsler, 1 Wooleys Lane, Great Neck, N.Y. 11023

[21] Appl. No.: 148,011

[22] Filed: Jan. 25, 1988

[51] Int. Cl.$^4$ .......................... G01F 1/22; G01F 1/28; G01N 11/12
[52] U.S. Cl. ..................................... 73/861.57; 73/57; 73/861.71
[58] Field of Search ........... 73/861.55, 861.56, 861.57, 73/57, 861.71; 116/273, 276

[56] References Cited

U.S. PATENT DOCUMENTS

| | | | |
|---|---|---|---|
| 1,631,746 | 6/1927 | Luckey | 73/57 |
| 2,431,378 | 11/1947 | Eitzen et al. | 73/57 |
| 2,618,974 | 11/1952 | Gilbert | 73/861.57 |
| 2,970,561 | 2/1961 | Ashwood | 116/273 |
| 4,227,409 | 10/1980 | Bingler | 73/861.71 |
| 4,517,830 | 5/1985 | Gunn | 73/57 |

FOREIGN PATENT DOCUMENTS

| | | | |
|---|---|---|---|
| 107843 | 10/1967 | Denmark | 73/861.71 |
| 933172 | 8/1955 | Fed. Rep. of Germany | 73/57 |
| 0235915 | 5/1986 | Fed. Rep. of Germany | 73/861.71 |
| 255590 | 3/1970 | U.S.S.R. | |

OTHER PUBLICATIONS

Kontes, "Flowmeters for Labratory & Industrial Use", catalog 8/63, pp. 1 and 7.

Primary Examiner—Herbert Goldstein

[57] ABSTRACT

A float for use in a fluid measurement device, symmetric about a central axis and containing an aperture along the axis which may be sized differently according to each float. When used in a rotameter type flowmeter, greater range and sensitivity in readings is permitted as compared to standard floats, by allowing fluid an additional orifice through which to pass. The improved float also allows multiple ranges of viscosity to be measured when used within a falling float type viscosimeter by selection of different size float apertures.

2 Claims, 1 Drawing Sheet

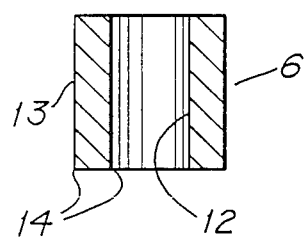
FIG. 1
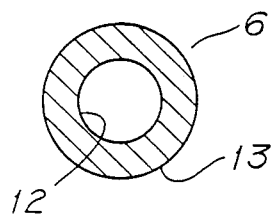
FIG. 2
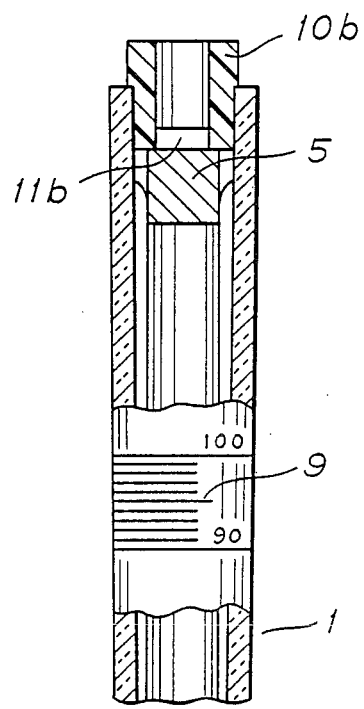
FIG. 3
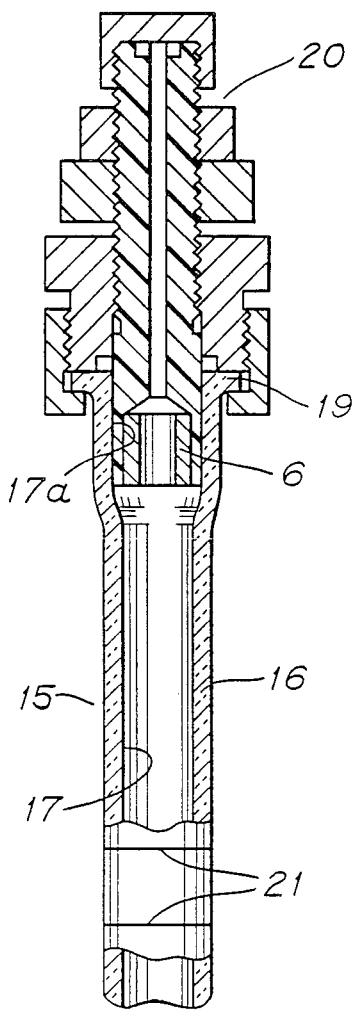
FIG. 4
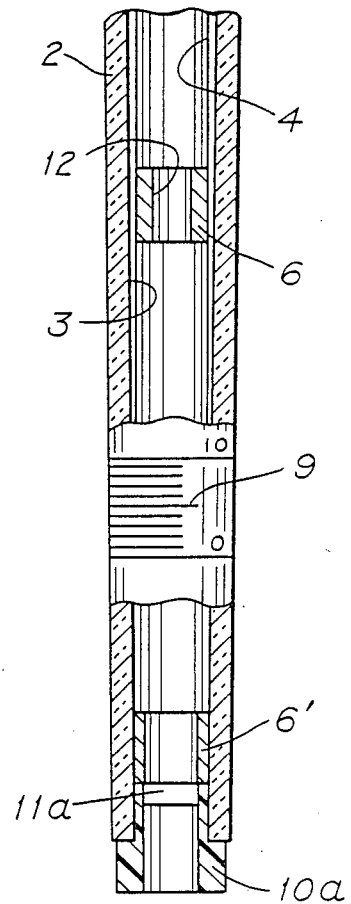
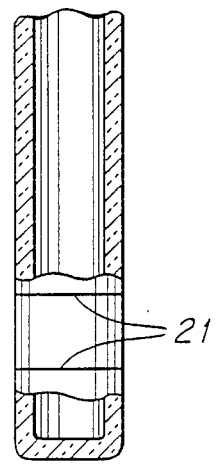

FLOAT FOR FLUID MEASUREMENTS

BACKGROUND OF THE INVENTION

The present invention relates to floats used in fluid flow measuring devices and more particularly to those devices such as rotameter type flowmeters, falling float viscosimeters, etc.

Many devices designed to measure various fluid parameters incorporate a captive float member as an integral part. Interaction between the test fluid and the float yields data which may then be converted into the physical property sought. Instruments used in the measurement and control of flowrates, and those designed to determine the physical characteristics of the fluid, such as viscosity, are among the more common and economically important applications.

A flowmeter of the variable area type, otherwise known as a rotameter, consists of an internally tapered tube positioned such that the larger diameter is at the top. A plummet or metering float, with a diameter slightly less than the minimum inside diameter of the tube is placed within the tube such that any clearance between the float and tube forms an annular orifice, with a cross sectional area which varies in accordance with the position of the float. The stream of fluid to be measured is made to enter the lower end of the tube and causes the float to rise to a height where its weight is just balanced by the pressure drop across the constriction. The tube is typically of glass or other suitable materials imprinted with a graduated scale such that the position of the float may be correlated with flow rate of the particular fluid under test.

In addition to being dependant on the nature of the fluid, the range of flowrates that a particular rotameter is capable of measuring is determined by its physical characteristics; namely, the size and weight of the float and the cross sectional area of the annular space formed by the float and the inside wall of the tube. To date, various attempts have been made to increase the useful range of a rotameter by manipulation of its dimensions. Increasing the weight of the float, by selecting materials of greater density, is one way of increasing the range of a given flowmeter. This method, however, achieves the increased capacity by compressing the entire range, thereby decreasing the accuracy of a particular reading. An additional problem arises in applications involving the metering of corrosive substances, where there is a limitation as to the type of materials that may be allowed to contact the fluid stream. Another way to create a flowmeter capable of handling a wider range of flowrates is to increase the degree of taper over the length of the tube. This method also serves to compress the range, resulting in decreased accuracy. In addition, increasing the taper beyond a certain point introduces increased costs of production by requiring the employment of more expensive manufacturing methods.

Where high rates of flow are to be measured, a bypass metering system is often used in order to limit the size of the rotameter. In such a system, the fluid stream is divided, allowing only a measured fraction of total flow through the rotameter, and the remainder bypassed through a chamber capable of handling larger volumes of flow than the rotameter. Inlet and outlet orifices control the percentage of total flow allowed to enter the rotameter itself. Despite being a useful means of measuring large volumes of flow, bypass flowmeters introduce a greater pressure drop to a system than a conventional rotameter alone due to the presence of the orifices.

Similar in construction and theory to a rotameter are viscosimeters of the falling-float type, and are widely used in determining fluid viscosity. Such devises consist of a float member within a precision bore tube of constant internal diameter. The float, with a smaller diameter than the inside diameter of the tube, describes an annular orifice of constant cross sectional area, independent of the position of the float within the tube. The tube itself is closed at one end and is generally equipped with internal stabilizing beads or flats to insure that the float remains centered within the tube during operation in a vertical position. During measurement, the tube is positioned such that the closed end is at the bottom. The top of the tube consists of a release mechanism which retains the float until a reading is to be taken. The tube is filled with the fluid to be tested, and the float is released. The float accelerates until it reaches a constant rate of speed, referred to as the terminal velocity. Time of decent is measured as it transverses a given distance, indicated by reference lines which are marked on the tube. As the float travels downward, it displaces a given volume of fluid which is forced to flow upward, past the float. Equations of flowrate governing flow through orifices may then be applied to determine the viscosity of the fluid.

To date, in order to insure that the float would travel at the terminal velocity for the entire length of travel between the reference lines, and at a rate of speed convenient for measuring, a different diameter tube was required for each particular range of viscosities.

Accordingly, the present invention provides an improved float capable of measuring an increased range of flowrates while also providing improved accuracy, when used in a rotameter type flowmeter, and provides a means of measuring an increased range of viscosities when used in a falling float type viscosimeter.

Another object is to provide these improved characteristics while also allowing the complete instrument to be compact and economical.

SUMMARY OF THE INVENTION

Briefly stated the invention consists of a cylindrically shaped float constructed of suitable material, with a coaxially and centrally positioned, precision-bore aperture of uniform inside diameter. Selection of different size apertures determines the range of the instrument in which the particular float is used by defining an additional orifice through which the fluid may pass.

When used in a rotameter, the unique design allows the same rotameter to measure multiple ranges of flowrates. A useful feature of the present design is that the pressure drops across the float during operation, remains a virtual constant independent of the diameter of the aperture, simplifying correlation of the flowmeter when used with a variety of fluids.

In a preferred embodiment a number of float members, each with a different diameter aperture, are placed within the flowmeter tube, in order of aperture size, with the float containing the largest orifice in the lowest position and the float with no aperture in the top position. The floats are designed in such a way that as each float reaches the upper limits of its travel in the tube, the succeeding float begins to rise within the tube, defining a higher consecutive range of flowrates.

In a preferred embodiment incorporating the present invention in viscosity measurement device, the float is placed within a falling float type viscosimeter. Unlike standard viscosimeters of this type in which fluid is forced around the float as it is displaced by the falling float, the present embodiment relies solely on fluid flow through the coaxially positioned aperture. Stabilizing beads are no longer necessary since the outer tube is constructed of precision bore tubing with an inside dimension only slightly larger than the outside diameter of the floats to be used. Multiple ranges of viscosity measurements are accomplished by varying the inside diameter of the particular float, rather than having to construct a new outer tube.

BRIEF DESCRIPTION OF THE DRAWINGS

FIG. 1 is an axial cross sectional view of a typical float member;

FIG. 2 is a cross sectional end view of the float member shown in FIG. 1.

FIG. 3 is a fragmentary axial cross sectional view of a flowmeter incorporating the present float design, with several floats in place, being shown in the typical position they assume during flow measurement;

FIG. 4 is an axial cross sectional view of a falling float type viscosimeter wherein the float member is shown held in place by the release mechanism prior to the taking of a measurement.

DETAILED DESCRIPTION OF THE PREFERRED EMBODIMENT

Referring now to the drawings, and in particular FIGS. 1 and 2, therein illustrated is a typical float member according to the present invention, generally designated 6. The float 6 is formed of glass or other suitable material, and is cylindrical in appearance, provided with a precision bore aperture 12. The outer wall 13 of the float 6 is also precision ground to a precise uniform diameter. The ends of the float 6 are cut flat and provided with fine chamfers 14.

Referring now to FIG. 3 therein illustrated is a rotameter incorporating float members according to the present invention, generally designated 1. The flowmeter 1 comprises a tube 2 formed of glass or other suitable material, said tube being generally cylindrical and provided with an axially tapered bore 3, the diameter of which is larger at the upper end and smaller at the lower end of said tube 2. Additionally, the inner surface of tube 2 is provided with circumferentially spaced, inwardly projecting beads 4 extending for the greater part of the length thereof. The inner surfaces of the beads 4 are parallel to the axis of the bore 3 and define a raceway of constant diameter. Received within the tube 2 are a number of float members 5, 6, and 6' cylindrically shaped and having an outside diameter slightly smaller than the diameter of the raceway formed by the beads 4. The beads 4 thus serve to maintain the float members 5, 6, and 6' in the center of the tube 2 and prevent excessive wobbling from side to side, while allowing complete freedom of movement vertically. Disposed on the outer surface of the tube 2 are scale divisions 9 through which the various float members 5, 6, and 6' are visible and thus facilitate the accurate determination of their respective positions along the length of the bore 3. The reading, in terms of graduations on the scale 9, correlate a given height in the tube 2 to a particular flowrate.

At the top and bottom of the tube 2 are plug members generally designated 10a and 10b. They are constructed of self-lubricating plastic material, preferably polytetrafluoraethylene (Teflon), and are sized to be a press-fit into both ends of the bore 3. An enlargement of the outside diameter of plugs 10a and 10b allow them to be inserted only a measured distance into the tube 2. Across the inwardly facing portions of the plugs 10a and 10b, slots 11a, 11b are provided to allow fluid to flow past the plugs 10a and 10b when the uppermost float member 5 reaches the uppermost limit of its travel or when flow is too small to lift the floats from their position of rest at the bottom of the tube 2.

Each of the float members 5, 6, and 6' are designed to measure a particular range of flowrates. The uppermost float member 5 is a solid cylinder which allows fluid to flow only between the tube 2 and the float 5. Each of the other floats 6, and 6' are provided with different diameter precision bore apertures 12, allowing fluid to flow not only around, but also through the float members 6, and 6'. The diameters of the aperture 12 are of such dimensions to allow each float 5, 6, and 6' to measure a consecutive range of flowrates. The larger the diameter of the aperture 12, the greater the flowrate required to suspend the float member 5, 6, and 6' at a particular scale division 9 within the tube 2 since increasing the aperture 12 provides a greater cross sectional area through which fluid may flow. The uppermost float member 5 having no aperture 12 requires the least amount of flow to cause it to rise within the tube 2 and therefore covers the lowest range of flowrates. During the entire range of travel of the solid float member 5 the other floats 6, and 6' remain at rest as a consequence of the apertures 12 which provide a less restricted path of flow.

Referring now to FIG. 4, therein illustrated is a device for measuring fluid viscosity which incorporates the float members according to the present invention, generally designated 15. The viscosimeter 15 is of the falling float type and comprises a tube 16 with a precision axial bore 17 of uniform diameter. The bore 17a is enlarged to a uniform inner diameter at one end and the tube 16 is provided with an outward extending flange 19 at the same end. The tube 16 is sealed at the other end. Received within the tube is a float 6, cylindrically shaped and having an outside diameter slightly smaller than the diameter of the bore 17.

Attached to the flange 19 at the open end of the tube 16 is a release mechanism 20. The release mechanism 20 may be adjusted such that the float 6 is held in place at the top of tube 16. When a measurement is to be taken, the release mechanism 20 is re-adjusted and the float 6 is released and allowed to fall vertically within the tube 16. Reference lines 21 on the tube 16 indicate a distance of travel and by measurement of the time of descent of the float 6 falling freely through this given distance in a vertical position, the viscosity of the fluid under test may be determined.

Although only a few embodiments of the present invention have been disclosed herein in detail, various modifications thereon will become apparent to those skilled in the art. Accordingly, the spirit and scope of the invention is to be limited only by the appended claims.

Having thus described the invention, what is claimed is:

1. A flowmeter comprising a vertically disposed tube which is open at both ends and has a tapered bore and a plurality of members disposed within the bore, at least one of the members having an aperture coaxial with the bore, arranged so that the successive members of the plurality respond to different ranges of fluid flow rate through the tube and, for any flow rate within a selected range, one of the members is maintained at a position between the ends of the tube.

2. A flowmeter comprising a vertically disposed tube which is open at both ends and has a tapered bore and a plurality of apertured members coaxially disposed within the bore, the apertures in successive members from the uppermost to the lowermost of the plurality being of successively increasing total cross-sectional area to permit successively increasing fluid flow rates through the members so that the successive apertured members of the plurality respond to different ranges of fluid flow rate through the tube and, for any flow rate within a selected range, one of the members is maintained at a position between the ends of the tube.

* * * * *